(12) United States Patent
Gennadievich

(10) Patent No.: US 8,619,255 B2
(45) Date of Patent: Dec. 31, 2013

(54) LASER INDUCED BREAKDOWN SPECTROSCOPY

(75) Inventor: Polushkin Valery Gennadievich, Moscow (RU)

(73) Assignee: RHM Technologies, Inc., Portland, OR (US)

( * ) Notice: Subject to any disclaimer, the term of this patent is extended or adjusted under 35 U.S.C. 154(b) by 210 days.

(21) Appl. No.: 13/103,962

(22) Filed: May 9, 2011

(65) Prior Publication Data

US 2012/0262712 A1   Oct. 18, 2012

Related U.S. Application Data

(60) Provisional application No. 61/476,152, filed on Apr. 15, 2011.

(51) Int. Cl.
 *G01J 3/30* (2006.01)
(52) U.S. Cl.
 USPC .......................................................... 356/318
(58) Field of Classification Search
 USPC .......................................................... 356/318
 See application file for complete search history.

(56) References Cited

U.S. PATENT DOCUMENTS

| | | |
|---|---|---|
| 4,410,338 A | 10/1983 | Yamamoto et al. |
| 5,560,890 A | 10/1996 | Berman et al. |
| 6,771,368 B1 | 8/2004 | Chadwick |
| 6,869,544 B2 | 3/2005 | Chen et al. |
| 7,394,537 B1 | 7/2008 | Lindfors et al. |
| 7,821,634 B2 * | 10/2010 | Dillon et al. ............... 356/318 |
| 8,248,602 B2 * | 8/2012 | Miziolek et al. ........... 356/318 |
| 2007/0046934 A1 | 3/2007 | Roy |
| 2007/0140931 A1 | 6/2007 | Huang et al. |
| 2008/0101423 A1 | 5/2008 | Mirov et al. |
| 2009/0298193 A1 | 12/2009 | Kim et al. |

\* cited by examiner

*Primary Examiner* — Kara E Geisel
(74) *Attorney, Agent, or Firm* — Marger Johnson & McCollom PC

(57) ABSTRACT

A laser induced breakdown spectroscopy system includes a laser module having a laser source, a sample chamber, a spectrometer arranged to capture spectral data from the sample chamber, a voltage source attached to the sample chamber arranged to apply a voltage to the sample during capture, and a controller in communication with the spectrometer, the voltage source and the laser module to trigger the voltage source and the spectrometer during laser excitation of the sample. A method of operating a laser induced breakdown spectroscopy system includes applying a voltage to a set of electrodes arranged around a sample, striking the sample with a laser during a time interval in which the voltage is being applied to the electrodes, sampling spectral data from the sample after the sample is struck with the laser, and removing the voltage after the spectral data has been sampled.

17 Claims, 4 Drawing Sheets

LASER INDUCED BREAKDOWN SPECTROSCOPY

RELATED APPLICATIONS

This application is a continuation of and claims priority to U.S. Provisional Patent Application No. 61/476,152, filed Apr. 15, 2011.

BACKGROUND

Laser-Induced Breakdown Spectroscopy (LIBS) uses a highly energetic laser pulse as an excitation source. The laser forms a plasma that atomizes and excites samples. A spectrometer then analyzes light emitted from the excited sample and determines what elements are present.

Theoretically, a LIBS system can detect all elements, limited only by the power of the laser, the sensitivity and the wavelength range of the detector. In reality, detection limits result from the plasma excitation temperature, the amount of time the spectrometer needs to collect the light, and the strength of the light emitted by the elements during transition. These limits affect the system's ability to detect the elements present, reducing it sensitivity. Increasing the sensitivity of the system allows for more accurate measurements.

LIBS systems have some advantages in size and potential for portability over other spectroscopy systems. However, portability may have trade offs with regard to the amount of power available to the system, which in turn may affect the sensitivity. The ability to increase the sensitivity of the measurements without sacrificing portability has significant advantages in producing a portable, accurate detector for use in the field.

DETAILED DESCRIPTION OF THE EMBODIMENTS

Figure 1:
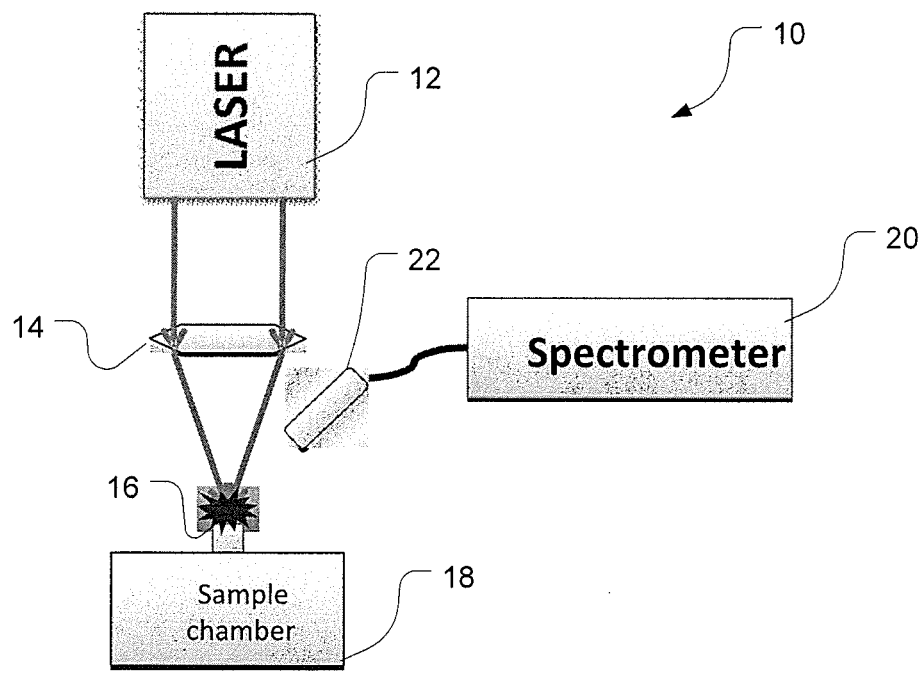
FIG. 1 shows a block diagram of an embodiment of a LIBS system.

FIG. 1 shows an embodiment of a LIBS (laser induced breakdown spectroscopy) system. In this embodiment, merely as an example, the system 10 includes a laser 12 that focuses through a lens 14 on a sample being tested 16. A sample chamber 18 contains the sample 16.

When the laser 12 focuses on the sample 16, it creates a plasma by ablating a very small amount of material from the sample, typically in the range of picograms to nanograms. The laser ablation generates a plasma plume having very high initial temperatures that then settle into thermodynamic equilibrium. As it settles into thermodynamic equilibrium, generally within microseconds, the plasma expands and cools, generating detectable emission lines. The detector 22 of the spectrometer 20 detects the characteristic atomic emission lines of the various elements present in the sample and the spectrometer analyzes them to produce a result.

In one embodiment, the laser uses an yttrium aluminum garnet (ND:$Y_3Al_5O_{12}$) laser element as its gain medium. For power savings purposes, the system may employ a passive Q-switch rather than an electro-optical or acoustic-optical Q-switch. Q-switching causes a laser to produce a pulsed output beam, allowing the laser to produce high peak power when compared to continuous output. Q-switching generally results from some sort of attenuation of the laser's optical resonator. The laser medium is pumped and the Q-switch is set to prevent feedback into the gain medium. Once the laser medium reaches some maximum level, the Q-switch is changed from low-Q to high-Q and the laser outputs a high peak intensity pulse of light.

Active Q-switching typically uses an externally controlled attenuator, such as a shutter, chopper, spinning mirror or an acousto- or electro-optic device. While these allow for faster transitions from low to high Q, they consume power and reduce the portability of the LIBS system. An alternative method uses a passive Q-switch.

A passive Q-switch generally involves some sort of absorber that can become saturated, a material in which transmission increases with the intensity of light exceeds some threshold. The material may include an ion-doped crystal, such as YAG:$CR^{+4}$ used with a YAG:Nd lasing element. By varying the laser's pump power and the amount of absorber in the cavity, one can control the pulse repetition rate.

Figure 2:
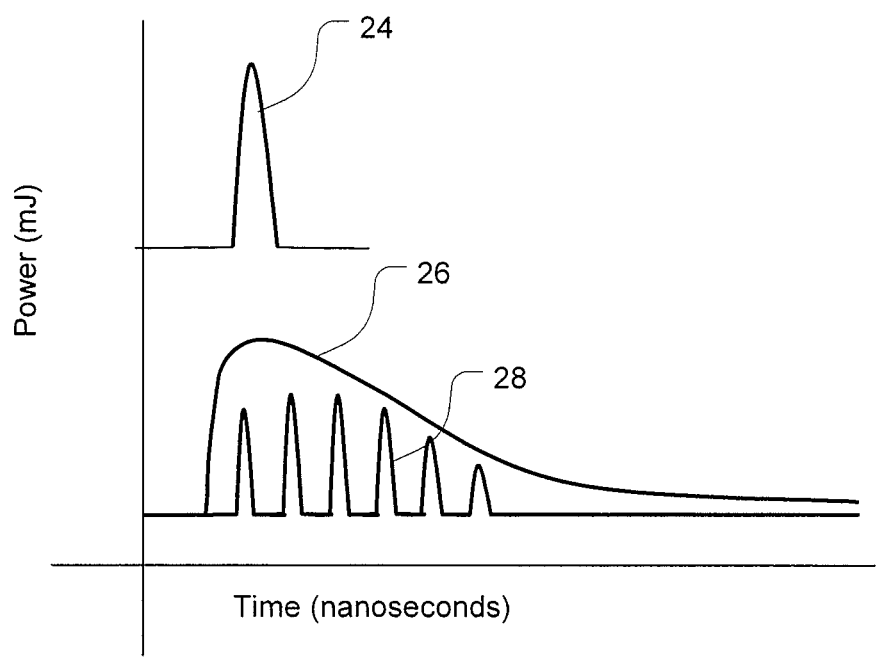
FIG. 2 shows a comparison of laser pulse waveforms for a LIBS system.

FIG. 2 shows a comparison of a typical LIBS laser output pulse to a LIBS laser output using a passive Q-switch. Trace 24 shows a typical LIBS laser output pulse, a short, single pulse of about 10 nanoseconds having a power output of 200 milliJoules (mJ). Trace 26 shows the shape of the flash lamp pumping pulse used to pump the laser. Trace 28 shows the shape of a pulse train using a passive Q-switch of YAG:$Cr^{+4}$ with a YAG:Nd laser. The resulting system has increased intensity of the plasma emission, which improves the sensitivity of measurement making the readings more accurate and capable of detecting smaller amounts of elements. The system also has a substantial improvement in the signal-to-noise ratio when compared to single pulse systems, also increasing the accuracy.

In addition to using a passive Q-switch to generate a pulse-train output, one may also consider using a different type of lasing element. Typically, the YAG:Nd laser using a YAG:$Cr^{+4}$ passive Q-switch has become one of the most popular systems for LIBS systems. This system emits light at a wavelength of about 1064 nanometers (nm).

However, one could employ a YAG:Er (erbium-doped YAG) emitting light at a wavelength of 2940 nm. This lasing element has better safety for eyes. In laboratory environments, protocols and safety procedures make laser injuries fairly uncommon. However, in a portable system used in the field that moves around may have heightened risk factors for injury. This lasing system at the broader wavelength has maximum absorption in water. This renders the system safer than other types of lasers, as if the laser were to strike a user's eye, the water in the user's eye would absorb the energy of the laser, avoiding damage to the eye.

In addition, the broader wavelength increases the sensitivity of the measurement. The broader wavelength increases the chances of detecting an element, because the chemical signatures of the elements spread out over the spectrum. The passive Q-switch for this system may use ZnSe:$Fe^{+2}$ (zinc selenium doped with iron ions), or YAG:$Fe^{+2}$ to achieve the pulse train discussed above.

Figure 3:
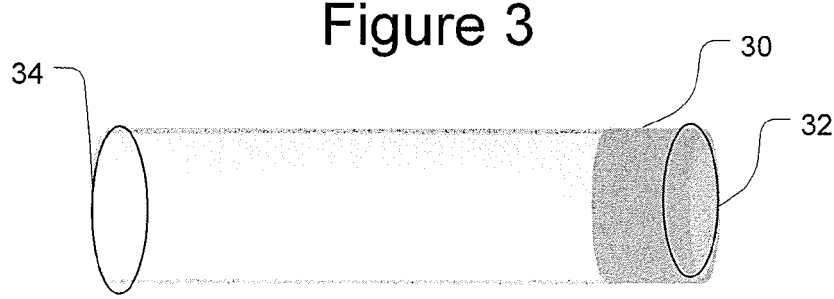
FIG. 3 shows an embodiment of a laser sample having integrated mirrors.

Further, to increase the system stability and to keep the dimensions of the system minimal for portability, one can coat the ends of the lasing element with mirrored coatings. In the embodiment of FIG. 3, the element 30, which may be any lasing element, has mirrored coatings 34 and 32. LIBS systems use mirrors to direct the light beam towards the sample chamber. In this embodiment, the mirrored coating 34 is a highly reflective mirror and the mirrored coating 32 is a low reflective mirror. The low reflective mirror passes the focused light to the sample chamber, focusing the light as it passes. In addition, one end of the lasing element may be convex, the other flat. This reduces losses that depend upon perpendicularity and parallelism of the end surfaces.

One issue that arises in laser systems in generally is the mirror alignment. Poorly aligned mirrors may result in the light becoming misdirected, reducing the operability of the system. This problem only increases when the system becomes portable and moves around. By using mirrored coatings on the elements, one avoids possible misalignment or maladjustment of mirrors, increasing the stability of the system.

Another improvement that can result in increased sensitivity of measurement involves increasing the duration and intensity of the plasma emission. This allows the detector to have more time to gather more information about elements that may exist in the sample in minute amounts. Without the extra time, the detector may not detect the smaller emissions of the smaller amounts of certain elements. This increase results from the application of a high-frequency, high-voltage source to the sample during laser ablation. LIBS plus high frequency (LHF™ or L+HF™) may result from placing electrodes on either side of the sample and activating them with a high-frequency, high-voltage (HVHF) pulse when the laser is applied.

Figure 4:
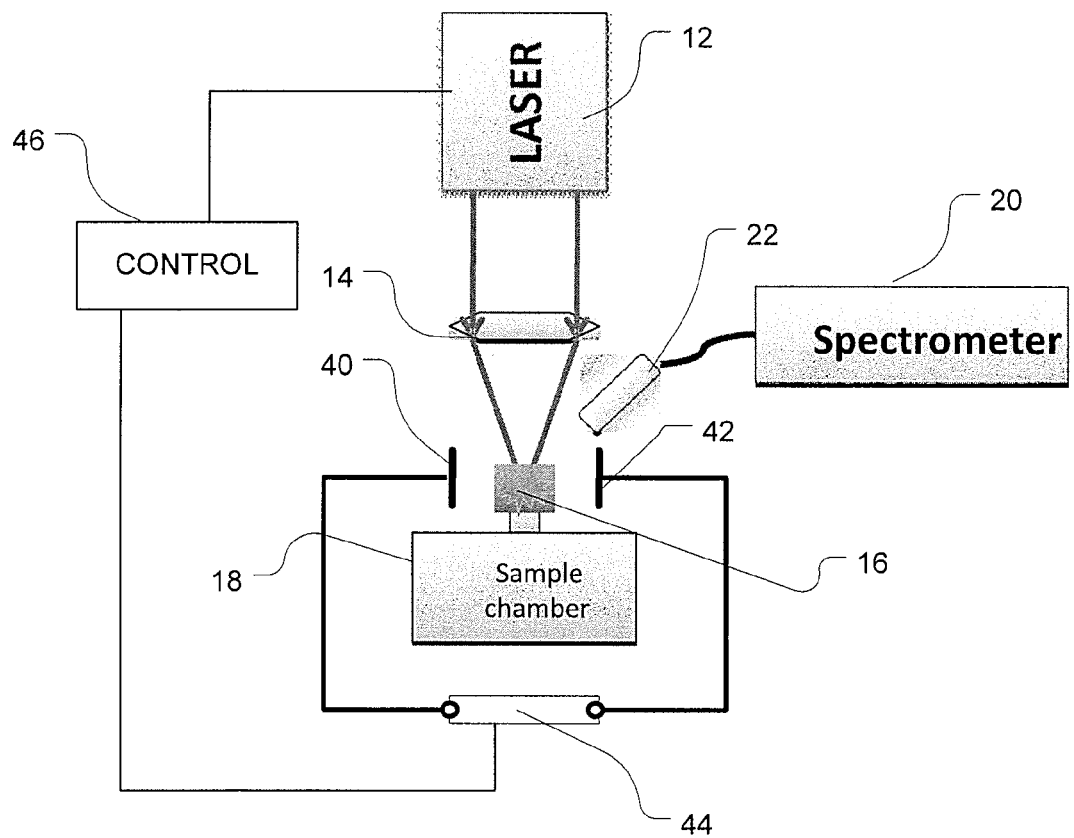
FIG. 4 shows an embodiment of a LIBS system having a high-frequency, high-voltage source.

FIG. 4 shows an embodiment of a LIBS system with a HVHF source and electrodes. In addition to the laser 12, lens 14, sample chamber 18, spectrometer 20 and detector 22, the system now includes electrodes 40 and 42, a HVHF power supply 44, and a controller 46. The controller manages the timing of the application of the HVHF pulse with the timing of application of the laser so that the sample has the HVHF pulse applied when being hit by the laser.

The controller also makes possible an automatic mode, in which the controller first turns on the high-frequency, high-voltage source and then the laser pulse, allowing for coordination between the two. In one embodiment, the electrodes receive a voltage signal in the range of 6-15 kV at a frequency of 100 KHz-4 MHz with a power of 5-100 W. The electrodes may be spaced apart by 5-8 millimeters, allowing a steady plasma in air or inert gas.

Figure 5A:
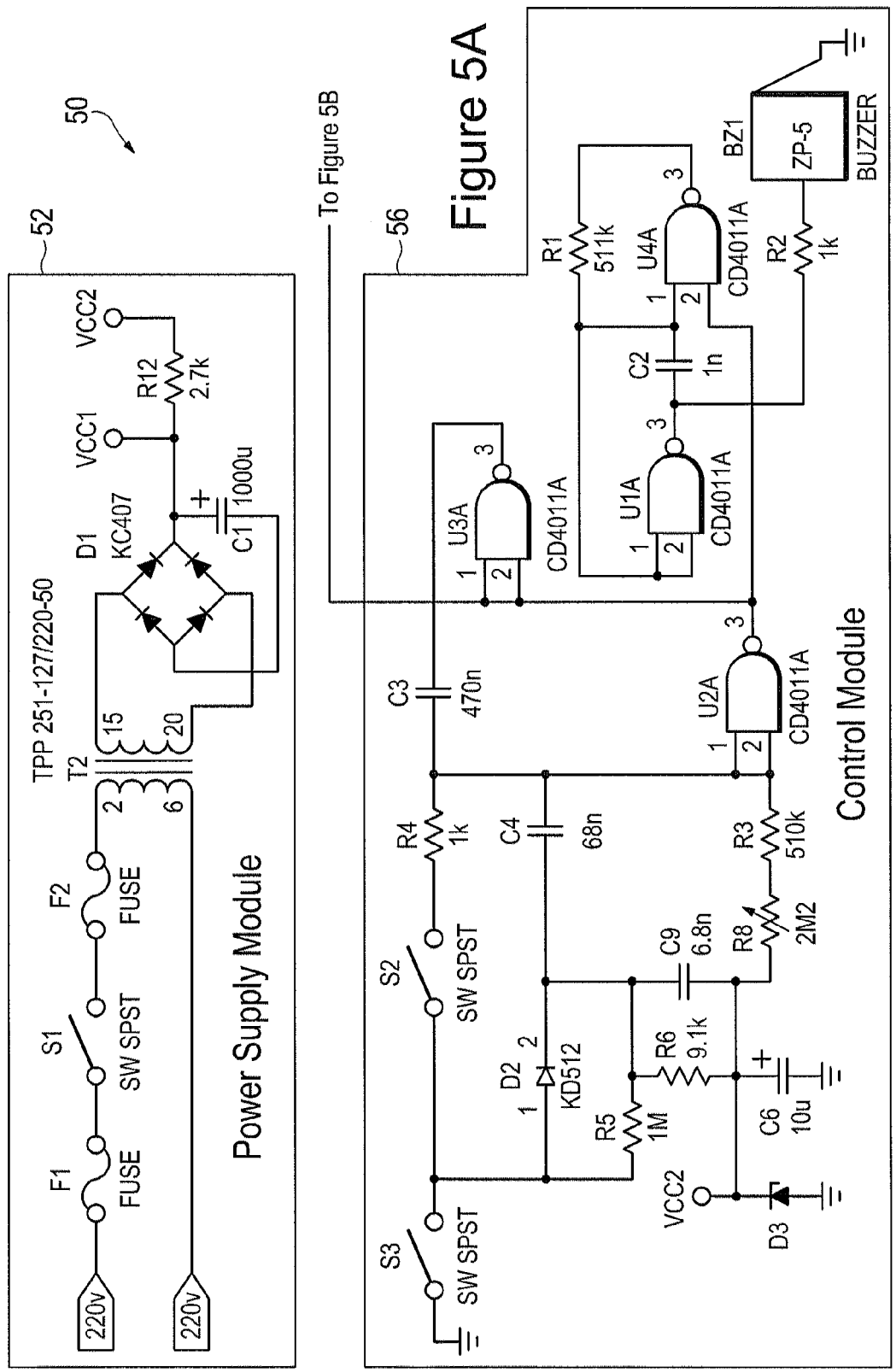
FIGS. 5A and 5B show an embodiment of an electrical circuit to produce a high-frequency, high-voltage source.
Figure 5B:
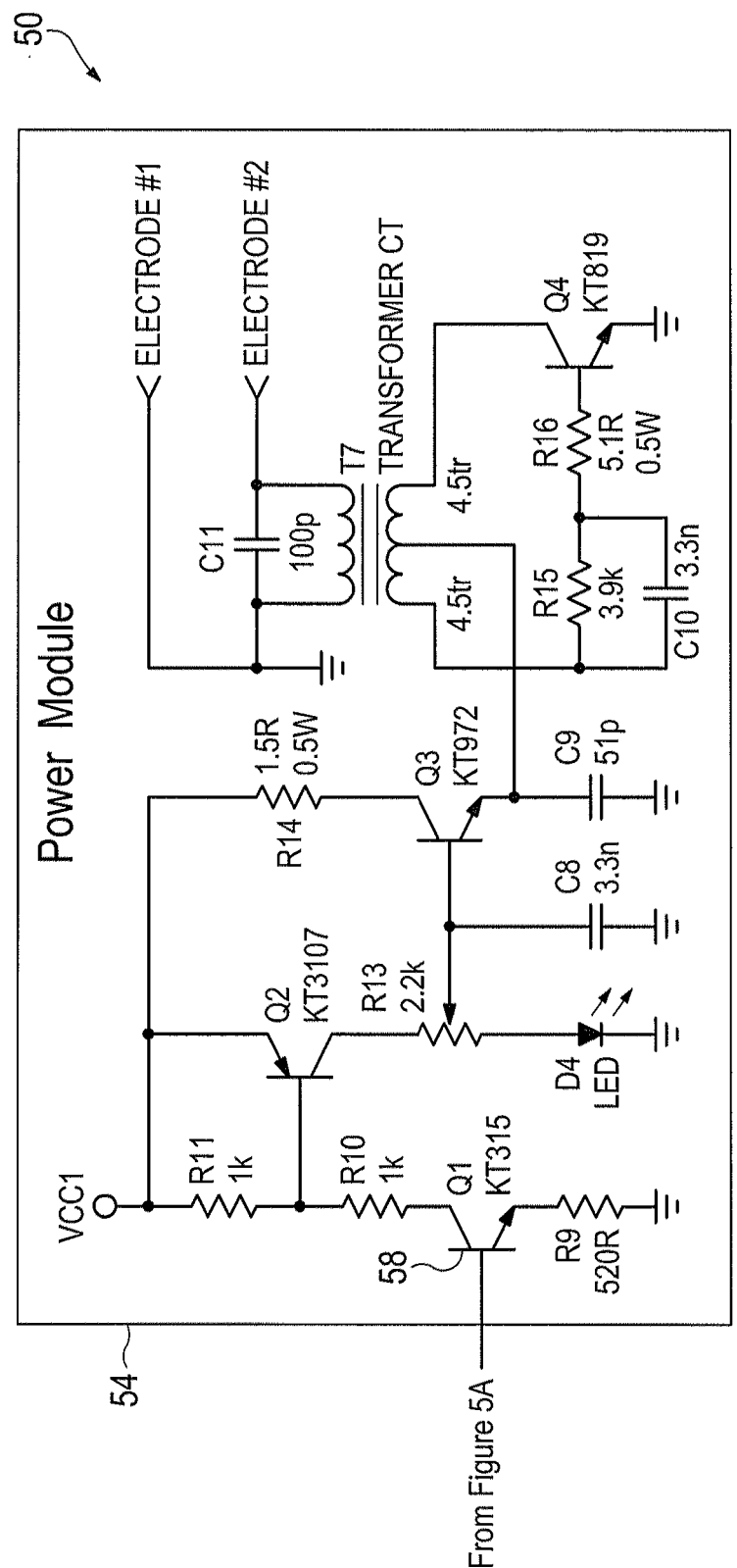

FIGS. 5A and 5B show an embodiment of a circuit that includes the power supply and the coordination of the laser pulse with the HFHV signal. The circuit 50 includes a power supply module 52, a control module 56 and a power module 54. The control module 56 receives the VCC2 voltage and generates a signal that is received by the power module 58 at transistor Q1 operating as a switch to pass VCC1 to the electrodes in the control module. This circuitry is merely an example of a high-frequency, high-voltage source and should not be viewed as a limitation to any particular embodiment.

The period of time in which to make the detection remains one of the issues in measurement sensitivity. The detector must be very 'fast' in that it must detect the characteristic emission lines during the microseconds in which they are present. One advantage of using the electrodes is that they extend this period of time, giving the detector more time to respond.

Thus, although there has been described to this point a particular embodiment for a method and apparatus for renewable security transactions in a SNAP environment, it is not intended that such specific references be considered as limitations upon the scope of this invention except in-so-far as set forth in the following claims.

What is claimed is:

1. A laser induced breakdown spectroscopy system, comprising:
    a laser module having a laser source;
    a sample chamber;
    a spectrometer arranged to capture spectral data from the sample chamber;
    a high-voltage, high-frequency source attached to the sample chamber arranged to apply a voltage to the sample during capture, wherein the high-voltage, high-frequency source has voltage in the range of 6 to 15 kilovolts, and operates at a frequency in the range of 100 Kilohertz to 4 Megahertz; and
    a controller in communication with the spectrometer, the voltage source and the laser module to trigger the voltage source and the spectrometer during laser excitation of the sample.

2. The system of claim 1, wherein the voltage source produces a voltage having a power of 5 to 100 Watts.

3. The system of claim 1, wherein the voltage source comprises a set of electrodes spaced apart on either side of a portion of the sample chamber such that the sample would reside between the electrodes.

4. The system of claim 1, wherein the laser module includes a passive Q-switch.

5. The system of claim 4, wherein the passive Q-switch comprises an absorber.

6. The system of claim 5, wherein the absorber comprises an yttrium aluminum garnet: chromium+4 ($YAG:Cr^{+4}$) absorber and the laser source comprises an yttrium aluminum garnet: neodymium gain element.

7. The system of claim 5, wherein the absorber comprises a zinc selenium iron absorber ($ZnSe:Fe^{+2}$) and the laser course comprises an yttrium aluminum garnet: erbium gain element ($YAG:Er^{+3}$).

8. The system of claim 5, wherein the absorber comprises an yttrium aluminum garnet: iron ($YAG:Fe^{+2}$) and the laser source comprises an yttrium aluminum garnet: erbium gain element ($YAG:Er^{+3}$).

9. The system of claim 1, wherein the laser source comprises a lasing element having first and second ends, the first end having a high reflective coating, wherein the high reflective coating reflects substantially all light impinging the high reflective coating and the second end having a low reflective coating transmitting substantially all light impinging the low reflective coating.

10. The system of claim 1, wherein the laser source includes an yttrium garnet aluminum: neodymium gain element ($YAG:Nd^{+3}$).

11. The system of claim 1, wherein the laser source includes an yttrium garnet aluminum: erbium gain element ($YAG:Er^{+3}$).

12. A laser induced breakdown spectroscopy system, comprising:
    a laser module having a laser source, the laser source having an yttrium garnet aluminum:
    erbium gain element and a passive Q-switch, the gain element having at least partially mirrored coatings at each of two ends of the gain element;
    a sample chamber;
    a spectrometer arranged to capture spectral data from the sample chamber;
    a high-voltage, high-frequency voltage source attached to a set of electrodes in the sample chamber, the voltage source arranged to apply a voltage in the range of 6 to 15 Kilovolts having a frequency in the range of 100 Kilohertz to 4 Megahertz to the sample during capture; and a controller in communication with the spectrometer, the voltage source and the laser module to trigger the voltage source and the spectrometer during laser excitation of the sample.

13. The system of claim 12, wherein the passive Q-switch comprises an absorber.

14. The system of claim 13, wherein the absorber comprises one of yttrium garnet aluminum: iron (YAG:$Fe^{+2}$) or zinc selenium: iron (ZnSe:$Fe^{+2}$).

15. The system of claim 12, wherein the voltage has a power of 5 to 100 Watts.

16. The system of claim 12, wherein the electrodes are arranged on either side of a gap in which the sample would reside, the gap having a width in the range of 5 to 8 millimeters.

17. A method of operating a laser induced breakdown spectroscopy system, comprising:

applying a high-voltage, high-frequency voltage in the range of 6 to 16 kilovolts operating at a frequency in the range of 100 kilohertz to 4 Megahertz to a set of electrodes arranged around a sample;

striking the sample with a laser during a time interval in which the voltage is being applied to the electrodes;

sampling spectral data from the sample after the sample is struck with the laser; and removing the voltage after the spectral data has been sampled.

* * * * *